(12) United States Patent
Leesman

(10) Patent No.: US 6,630,161 B1
(45) Date of Patent: Oct. 7, 2003

(54) ADJUVANT COMPOSITION AND METHODS FOR ITS USE

(75) Inventor: Glen D. Leesman, Hamilton, MT (US)

(73) Assignee: Ribi Immunochem Research, Inc., Hamilton, MT (US)

( * ) Notice: Subject to any disclaimer, the term of this patent is extended or adjusted under 35 U.S.C. 154(b) by 0 days.

(21) Appl. No.: 09/307,321

(22) Filed: May 7, 1999

Related U.S. Application Data
(60) Provisional application No. 60/084,678, filed on May 7, 1998.

(51) Int. Cl.[7] .......................... A61K 9/66; A61K 9/127; A61K 45/00; A61K 47/44; A61K 33/08
(52) U.S. Cl. .................... 424/455; 424/450; 424/283.1; 424/690; 424/689
(58) Field of Search ................................ 424/455, 450, 424/283.1, 690, 689, 698

(56) References Cited

U.S. PATENT DOCUMENTS

| | | | | |
|---|---|---|---|---|
| 4,258,029 A | * | 3/1981 | Moloney et al. | |
| 4,436,727 A | * | 3/1984 | Ribi | |
| 4,857,318 A | * | 8/1989 | Lee | |
| 4,912,094 A | * | 3/1990 | Myers et al. | |
| 5,026,557 A | * | 6/1991 | Estis et al. | |
| 5,312,620 A | * | 5/1994 | Ribi | |
| 5,324,512 A | | 6/1994 | Ladd et al. | |
| 5,376,369 A | * | 12/1994 | Allison et al. | 424/278.1 |
| 5,387,421 A | * | 2/1995 | Amidon et al. | |
| 5,422,109 A | * | 6/1995 | Brancq et al. | 424/184.1 |
| 5,616,331 A | * | 4/1997 | Allard et al. | 424/401 |
| 5,626,873 A | * | 5/1997 | Weiner et al. | 424/455 |
| 5,670,139 A | * | 9/1997 | Allard et al. | 424/59 |
| 5,709,879 A | * | 1/1998 | Barchfeld et al. | |
| 5,716,637 A | * | 2/1998 | Anselem et al. | |
| 5,733,572 A | * | 3/1998 | Unger et al. | |
| 5,773,011 A | * | 6/1998 | Grubhofer | |
| 5,858,334 A | * | 1/1999 | Ascione et al. | 424/59 |
| 5,858,398 A | * | 1/1999 | Cho | 424/450 |
| 5,948,769 A | * | 9/1999 | Ismail | |
| 5,961,970 A | * | 10/1999 | Lowell et al. | |
| 5,985,284 A | * | 11/1999 | Lowell | |
| 5,989,583 A | * | 11/1999 | Amselem | |
| 5,997,888 A | * | 12/1999 | Weder et al. | |
| 6,110,492 A | * | 8/2000 | Alving et al. | |
| 6,113,941 A | * | 9/2000 | Takada et al. | |
| 6,288,026 B1 | * | 9/2001 | Exner et al. | 514/2 |
| 6,299,884 B1 | * | 10/2001 | Van Nest et al. | 424/283.1 |
| 6,316,545 B1 | * | 11/2001 | Sakuta | 524/837 |
| 6,451,325 B1 | * | 9/2002 | Van Nest et al. | 424/283.1 |
| 6,514,503 B1 | * | 2/2003 | Gizurarson et al. | 424/278.1 |

FOREIGN PATENT DOCUMENTS

| | | | |
|---|---|---|---|
| EP | 0 868 918 A | | 10/1998 |
| JP | 57 206625 A | | 12/1982 |
| WO | WO 89/06955 | * | 8/1989 |
| WO | WO 96 14871 A | | 5/1996 |
| WO | 99/56776 | * | 11/1999 |

OTHER PUBLICATIONS 59,161,313, 1993, Japan.*
09,241,152, 1997, Japan, Morimoto et al.*
Katz et al, FEMS Microbiology Immunology, 76:305–320, 1991.*
Alving, Journal Immunological Methods, 140;1–13, 1991.*
Gupta et al, Vaccine, 11/3:293–306, 1993.*
Alving et al, Immunology Letters, 25:275–280, 1990.*
Alving et al, Vaccine, 4:166–172, 1986.*

* cited by examiner

Primary Examiner—Nita Minnifield
(74) Attorney, Agent, or Firm—Townsend and Townsend and Crew LLP

(57) ABSTRACT

An adjuvant composition which is a stable oil-in-water emulsion comprising a metabolizable oil, one or more surfactants, an antioxidant and a compound to make the emulsion isotonic is described and claimed. The stable emulsion has a hydrophobic-lipophilic balance (HLB) of from about 7.5 to about 10.5 and a particle size of less than 3 µm.

In a preferred embodiment, the stable emulsion comprises 10% volume to volume squalene, 0.09% weight to volume PLURONIC F-68 block co-polymer, 1.9% weight to volume egg phosphatidyl choline, 1.75% volume to volume glycerol and 0.05% weight to volume α tocopherol. The preferred emulsion has a HLB of 8.0 and a particle size of about 0.2 µm. In a particularly preferred embodiment, the stable emulsion is combined with an attenuated lipid A derivative such as monophosphoryl lipid A or 3-deacylated monophosphoryl lipid A to enhance the adjuvanticity of the composition.

7 Claims, No Drawings

ADJUVANT COMPOSITION AND METHODS FOR ITS USE

This application claims the benefit of Ser. No. 60/084,678 filed May 7, 1998.

BACKGROUND OF THE INVENTION

Vaccines comprise antigens or combinations of antigens which when administered to a warm-blooded animal prevent, ameliorate or treat disease. Vaccines for.infectious diseases originally comprised whole, attenuated or killed microbes. It was soon discovered however that only a few proteins or protein fragments of a microbe or cell stimulated a protective immune response, and, in fact, inclusion of extraneous materials from the whole cell could hinder the immune response. Therefore, vaccine development focused on identifying the particular protein, protein fragment, epitope and DNA segment encoding that epitope which elicited the protective immune response. As antigen identification became more precise however, vaccine efficiency declined. Identified: antigens were often small molecules unable to be recognized by antigen processing cells. It was therefore necessary to combine these antigens with substances which enhance the antigenicity of the antigen and give a superior immune response. These substances are adjuvants.

Adjuvants work by several means. Some assist in the presentation of antigen to antigen processing cells (APC). Oil-in-water emulsions, water-in-oil emulsions, liposomes and microbeads each assist in presenting antigen to APC. Small antigens or haptens are often linked to larger, immunogenic proteins or polysaccharides to facilitate recognition by the APC. Certain adjuvants have a depot effect holding antigen in place until the body has an opportunity to mount an immune response. Other adjuvants stimulate the immune system generally augmenting the specific response mounted to the antigen.

The attenuated lipid A derivatives (ALD) monophosphoryl lipid A (MLA) and 3-deacylated monophosphoryl lipid A (3D-MLA) are potent immunological adjuvants used in prophylactic vaccines for infectious disease and therapeutic vaccines for the treatment of cancerous tumors and chronic infections. MLA and 3D-MLA are modified forms of the bacterial endotoxin lipopolysaccharide (LPS) and are known and described in U.S. Pat. Nos. 4,436,727 and 4,912,094, respectively. MLA and 3D-MLA induce both a humoral antibody response and a cell-mediated immune response in patients administered the compounds with an antigen.

An effective vaccine presents antigens to a warm-blooded animal such that the animal can mount a protective immune response to those antigens. Often, a vaccine composition must include an adjuvant to achieve this effect. Adjuvants which stimulate both a humoral and cellular immune response and are safe and non-toxic would promote the efficacy of any vaccine.

SUMMARY OF THE INVENTION

The subject invention is a novel adjuvant composition. The adjuvant composition is a stable oil-in-water emulsion (SE) comprising a metabolizable oil, surfactants, an antioxidant and a component to make the emulsion isotonic. The particle size of the claimed stable emulsion is less than 130 nm to 3 $\mu$m. Emulsions in the range of 70–200 nm can be sterilized by filtration. The hydrophobic-lipophilic balance (HLB) of the stable emulsion.is from about 7.5 to about 10.5 and preferably about 8.0.

In a preferred embodiment, the adjuvant composition is combined with an attenuated lipid A derivative (ALD). The addition of an ALD increases the adjuvanticity of the composition. ALDs useful according to the subject invention include monophosphoryl lipid A and 3-deacylated monophosphoryl lipid A. ALD can be included in the formulation at a concentration ranging from about 1 $\mu$g–12,000 $\mu$g/ml. Vaccine compositions of the novel stable emulsion are also claimed.

DETAILED DESCRIPTION OF THE INVENTION

The subject invention is an adjuvant composition which is a stable oil-in-water emulsion comprising a metabolizable oil, surfactants, an antioxidant and a component to make the emulsion isotonic. The resulting emulsion is buffered, has a particle size of less than 3 $\mu$m and a hydrophobic-lipophilic balance of the stable emulsion is from about 7.5 to about 10.5 and preferably about 8.0.

In a preferred embodiment the stable emulsion comprises from about 2% to about 15%, and preferably 10%, volume/volume of the metabolizable oil squalene. Surfactants are present in the stable emulsion at about 2%. Approximately 50 $\mu$g of an antioxidant can be added to the stable emulsion of the subject invention and approximately 1.75% of an agent to make the emulsion isotonic.

Meabolizable oils useful according to the subject invention include squalene, soybean oil, sesame oil and caprylic/capric acid triglycerides (MIGLYCOL 810 oil). Squalene is preferred.

Surfactants useful according to the subject invention are Tween 80, polysorbate 80 (CAPMUL POE-O low PV surfactant, ABITEC Corp., Janesville, Wis.), polyethylene 660 12-hydroxystearate (SOLUTOL HS15, BASF Corp., Chicago, Ill.) and poloxamer 188 (PLURONIC Q F68 block co-polymer, BASF Corp., Chicago, Ill.), sodium cholate, glycerodeoxy cholate, phosphatidyl choline, with poloxamer 188 being preferred. It was found that Tween 80 and polysorbate 80 surfactant produced a histamine type response when administered intravenously to dogs. Other suitable surfactants include sphingolipids such as sphingomyelin and sphingosine and phospholipids such as egg phosphatidylcholine, 1,2-Dimyristoyl-sn-glycero-3-phosphoethanolamine, L-$\alpha$-Phosphatidylethanolamine, and 1,2-Dipalmitoyl-sn-glycero-3-phosphocholine (DPPC) or mixtures thereof. DPPC is acceptable for use in humans.

Antioxidants useful in the stable emulsion of the subject invention include a tocopherol, and ascorbic acid, with $\alpha$ tocopherol being preferred.

Agents that can be added to the emulsion of the subject invention to make the adjuvant isotonic include dextrose, glycerol, mannitol, sorbitol, PEG 300, PEG 400 and polyethylene glycol, with glycerol being preferred.

In a particularly preferred embodiment, an attenuated lipid A derivative (ALD) is incorporated into the compositions of the subject invention. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay (CELD$_{50}$) ALDs useful according to the subject invention include monophosphoryl lipid A (MLA) and 3-deacylated monophosphoryl lipid A (3D-7MLA). MLA and 3D-MLA are known and need not be described in detail herein. See for example U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 U.S. Pat. No. 4,912,094 to Myers, et al., also assigned to Ribi ImmunoChem Research, Inc., embodies 3-deacylated monophosphoryl lipid A and a method for its manufacture. Disclosures of each of these patents with respect to MLA and 3D-MLA are incorporated herein by reference.

Without going into the details of the prior incorporated by reference patents, monophosphoryl lipid A (MLA) as used herein is derived from lipid A, a component of enterobacterial lipopolysaccharides (LPS), a potent but highly toxic immune system modulator. Edgar Ribi and his associates achieved the production of monophosphoryl lipid A (MLA) referred to originally as refined detoxified endotoxin (RDE). MLA is produced by refluxing an endotoxin extract (LPS or lipid A) obtained from heptoseless mutants of gram-negative bacteria in mineral acid solutions of moderate strength (0:1 N HCl) for a period of approximately 30 minutes. This treatment results in the loss of the phosphate moiety at position 1 of the reducing end glucosamine.

Coincidentally, the core carbohydrate is removed from the 6 position of the non-reducing glucosamine during this treatment. The resulting product (MLA) exhibits considerable attenuated levels of the endotoxic activities normally associated with the endotoxin starting material, such as pyrogenicity, local Shwarzman reactivity, and toxicity as evaluated in the chick embryo 50% lethal dose assay ($CELD_{50}$). However, it unexpectedly retains the functionality of lipid A and LPS as an immunomodulator.

Another detoxified endotoxin which may be utilized in the practice of the present invention is referred to as 3-deacylated monophosphoryl lipid A (3D-MLA). 3D-MLA is known as set forth in U.S. Pat. No. 4,912,094, reexamination certificate B1 U.S. Pat. No. 4,912,094, and differs from MLA in that there is selectively removed from the MLA molecule the B-hydroxymyristic acyl residue that is ester linked to the reducing-end glucosamine at position 3 under conditions that do not adversely affect the other groups. 3-deacylated monophosphoryl lipid A is available from Ribi ImmunoChem Research, Inc., Hamilton, Mont. 59840.

The MLA and 3D-MLA molecules are a composite or mixture of a number of fatty acid substitution patterns, i.e., heptaacyl, hexaacyl, pentaacyl, etc., with varying fatty acid chain lengths. Thus, various forms of MLA and 3D-MLA, including mixtures thereof, are encompassed by this invention. The lipid A backbone that is illustrated in U.S. Pat. No. 4,912,094 and reexamination certificate B1 U.S. Pat. No. 4,912,094 corresponds to the product that is obtained by 3-deacylation of heptaacyl lipid A from *S. Minnesota* R595. Other fatty acid substitution patterns are encompassed by this disclosure; the essential feature is that the material be 3-deacylated.

The modified 3D-MLA utilized in the present invention is prepared by subjecting MLA to alkaline hydrolysis under conditions that result in the loss of but a single fatty acid from position 3 of the lipid A backbone. β-hydroxymyristic fatty acid at position 3 is unusually labile in alkaline media. It requires only very mild alkaline treatment to completely 3-deacylate lipid A. The other ester linkages in lipid A require somewhat stronger conditions before hydrolysis will occur so that it is possible to selectively deacylate these materials at position 3 without significantly affecting the rest of the molecule. The reason for the unusual sensitivity to alkaline media of the ester-linked β-hydroxymyristic fatty acid at position 3 is not known at this time.

Although alkaline hydrolysis procedures are known, it is important to choose conditions that do not cause further hydrolysis beyond the ester linkage to the β-hydroxymyristic at position 3.

In general the hydrolysis can be carried out in aqueous or organic media. In the latter case, solvents include methanol (alcohols), dimethyl sulfoxide (DMSO), dimethylformamide (DMF), chloroform, dichloromethane, and the like, as well as mixtures thereof Combinations of water and one or more of the mentioned organic solvents also can be employed.

The alkaline base can be chosen from among various hydroxides, carbonates, phosphates and amine. Illustrative bases include the inorganic bases such as sodium hydroxide, potassium hydroxide, sodium carbonate, potassium carbonate, sodium bicarbonate, potassium bicarbonate, and the like, and organic bases such as alkyl amines, and include, but are not limited to, diethylamine, triethylamine, and the like.

In aqueous media the pH is typically between approximately 10 and 14 with a pH of about 12 to about 13.5 being the preferred range. The hydrolysis reaction is typically carried out at a temperature of from about 20° C. to about 80° C., preferably about 50° C. to 60° C. for a period of about 10 to about 30 minutes. For example, the hydrolysis can be conducted in 3% triethylamine in water at room temperature (22°–25° C.) for a period of 48 hours. The only requirement in the choice of temperature and time of hydrolysis is that deacylation occurs to remove only the α-hydroxymyristic at position 3.

In practice it has been found that a particularly desirable hydrolysis method involves dissolving lipid A or monophosphoryl lipid A in chloroform:methanol 2:1 (v/v), saturating this solution with an aqueous buffer consisting of 0.5M $Na_2CO_3$ at pH 10.5, and then flash evaporating the solvent at 45°–50° C. under a vacuum for an aspirator (approximately 100 mm Hg). The resulting material is selectively deacylated at position 3. This process can also be carried out with any of the inorganic bases listed above. The addition of a phase transfer catalyst, such as tetrabutyl ammonium bromide, to the organic solution prior to saturation with the aqueous buffer may be desirable in some cases. In addition to MLA and 3D-MLA produced as described above, ALD produced by synthetic or semi-synthetic processes may be used.

The composition of the subject invention is an adjuvant. When an effective amount of the composition is administered to a host with a protein antigen. The host's immune response to that antigen is enhanced. An effective amount of the claimed adjuvant composition is a quantity which stimulates or enhances an immune response. One skilled in the art would know the amount of antigen which is necessary to stimulate an immune response to that antigen. For example, 2.5 μg of hepatitis B surface antigen (HBsAg) administered with a preferred embodiment of the subject invention induced a humoral response in mice.

It has been unexpectedly found that the stable emulsion of the subject invention when combined with an ALD significantly reduces the pyrogenicity of the ALD. Pyrogenicity is the production of a febrile state by a compound. The ALD, 3D-MLA produces a higher febrile response when formulated in 40% polyethylene glycol, 10% ethanol than when formulated in the stable emulsion of the subject invention. Pyrogenicity of a composition can be evaluated in a standard three rabbit USP pyrogen test. Briefly, three rabbits are administered the compounds at varying doses. Each animal's body temperature is monitored over the course of 4 hours. Any temperature decrease is recorded as a rise of zero. An individual rise in temperature of less than 0.5° F. was considered non-pyrogenic. If the composition causes an individual rise in temperature of 0.5° F. or more, the composition is retested using five different rabbits. If not more than three of the eight total rabbits exhibited a rise in temperature of 0.5° F. or more and if the sum of the rise in temperature for each of the eight rabbits does not exceed 3.3° F., the composition is considered non-pyrogenic.

Following are examples which illustrate procedures for practicing the invention. All percentages are by weight and all solvent mixture proportions are by volume unless otherwise noted.

EXAMPLE 1

Preparation of 3D-MLA/SE

In a particularly preferred embodiment, the stable emulsion of the subject invention comprises the following:

| Material | Amount |
|---|---|
| 3D-MLA | 1.200–0.005% w/v |
| squalene | 10.000% v/v |
| PLURONIC-F68 block co-polymer | 0.091% w/v |
| Egg phosphatidyl choline | 1.909% w/v |
| glycerol | 1.800% v/v |
| α tocopherol | 0.050% w/v |
| Water for Injection | 78.200% v/v |
| ammonium phosphate buffer | 10.000% v/v |

It would be apparent to one skilled in the art how to prepare the claimed emulsion. However, we have found the claimed emulsion is most easily prepared by fixing three stock solutions: MLA/egg PC stock, oil stock solution and aqueous stock solution.

To prepare the MLA/egg PC stock, 3-deacylated monophosphoryl lipid A (3D-MLA) (Ribi ImmunoChem Research, Inc. Hamilton, Mont.) and egg phosphatidyl choline (egg PC) are each dissolved in 4:1 chloroform:methanol:(C:M). The solutions are then combined and the C:M is allowed to evaporate. Remaining C:M is removed by placing the mixture in a lyophilizer and holding it approximately 1–2 hours at a reduced pressure.

An oil phase stock solution is prepared by combining α tocopherol and squalene and swirling them in a heated water bath until dissolved.

An aqueous phase stock solution is prepared by weighing PLURONIC F-68 N block co-polymer and glycerol into a screw cap bottle. Water for Injection is added to the bottle which is warmed and mixed gently until the ingredients dissolve. 0.25 M ammonium phosphate buffer, pH 5.1±0.005 is added to the PLURONIC F-68 NF block co-polymer glycerol/water. Additional water is added to attain the desired volume.

To prepare the stable emulsion, the stock oil phase is combined with the MLA/egg PC mixture. The mixture is sonicated until the MLA is dissolved. The oil phase is then heated to 75° C. while the aqueous.phase is heated to 75° C. The oil phase MLA/egg PC mixture is emulsified with a Silverson Emulsifier,while the aqueous phase is added slowly. The resulting SE emulsion has an HLB of 8.0 and is cooled to room temperature in an ice bath. The emulsion can be further homogenized using an Avestin C-50 homogenizer at a pressure of 22,000–25,000 psi at the valve until the particle size is ≦0.2 μm. The final adjuvant product is filtered using a 0.2 μm hydrophilic membrane filter. The steps of further homogenization and terminal filter sterilization do not affect the amount of 3D-MLA present in the composition or the adjuvanticity of the preparation.

EXAMPLE 2

Generation of an Antibody Response Using 3D-MLA/SE

Mice were given a primary immunization (1°) of 2.5 μg hepatitis B surface antigen (HBsAg) formulated in the adjuvant as prepared in Example 1 on day 0. Injections were given subcutaneously (200 μl per injection). On day 21 the mice were given a secondary immunization (2°) administered (200 μl per injection). Mice were bled on day 19 following the primary immunization (day 19 post 1°) and day 27 following the secondary immunization (day 27 post 2°). Serum was collected and tested by standard ELISA for anti-HBsAg antibody. Table 1 shows that the adjuvant composition of the subject invention induced the production of anti-HBsAg antibodies in an animal when administered to the animal with that antigen.

TABLE 1

Anti-HBsAg antibody titers generated using 3D-MLA/SE

| | | | Anti-HBsAg Titer[-1] | | | |
|---|---|---|---|---|---|---|
| | | | $IgG_1$-Specific | | $IgG_{2a}$-Specific | |
| | Adjuvant | 3D-MLA μg | day 19 post 1° | day 27 post 2° | day 19 post 1° | day 27 post 2° |
| Pre-diluted 1/10 day7 | 3D-MLA/SE | 50 | 16 K* | 256 K | 64 K | 1000 K |
| | 3D-MLA/SE | 25 | 32 K | 512 K | 64 K | 1000 K |
| | 3D-MLA/SE | 5 | 16 K | 256 K | 16 K | 512 K |
| | 3D-MLA/SE | 1 | 8 K | 256 K | 16 K | 256 K |
| | SE (Vehicle) | 0 | 4 K | 128 K | 2 K | 64 K |
| | PBS | 0 | 2 K | 32 K | 2 K | 64 K |
| diluted 1/10 day0 | 3D-MLA/SE | 50 | 16 K | 256 K | 64 K | 1000 K |
| | 3D-MLA/SE | 25 | 16 K | 256 K | 64 K | 1000 K |
| | 3D-MLA/SE | 5 | 8 K | 128 K | 32 K | 512 K |
| | 3D-MLA/SE | 1 | 4 K | 128 K | 16 K | 256 K |
| | SE (Vehicle) | 0 | 2 K | 128 K | 1 K | 64 K |
| | PBS | 0 | 1 K | 128 K | 2 K | 32 K |
| | Normal Sera | — | <0.5 K | <0.5 K | <0.5 K | <0.5 K |

*K = $10^3$

EXAMPLE 3

Stimulation of a Cytotoxic T-lymphocyte Response

A) The induction of a cytotoxic T-lymphocyte (CTL) response after administration of the adjuvant composition of the subject invention and a protein antigen was detected by a cytotoxicity assay. Groups of C57/BL/6 mice were given a primary immunization subcutaneously (inguinal region) with 1.0 μg hepatitis B surface antigen (HbsAg) formulated in the stable emulsion vehicle of the subject invention (SE) and 3D-MLA/SE. MLA/SE adjuvant was prepared as in Example 1. To test stability of the claimed stable emulsion the emulsion was diluted 1/10 seven days prior to mixing it with the antigen or on the day of immunization. The injected volume was 200 μl. Fourteen days later three mice per experimental group were killed and spleens removed and pooled as single cell suspensions and counted. Mice remaining in each group were given a secondary immunization subcutaneously (inguinal region) with 1.0 μg HbsAg formulated in SE vehicle and 3D-MLA/SE adjuvant. Fourteen days later all mice in each experimental group were killed and spleen removed and pooled as single cell suspensions and counted.

Spleen cells ($75 \times 10^6$ cells in 3–4 ml media) from the experimental groups were placed in a 25 cm² T-flask. Next, 1.0 ml of irradiated (20,000 rads) E.G7 (OVA) cells at $5 \times 10^6$/ml were added to the flask. The volume was brought to 10 ml. The cultures were maintained by placing the T-flasks upright in a 37° C., 5% $CO_2$ incubator for four days. On day 4 the surviving cells were recovered from the flasks, washed 1×, resuspended in 5.0 ml, and counted.

Recovered effector cells were adjusted to $5 \times 10^6$ viable cells/ml and 100 μl volumes were diluted serially in triplicate in wells of 96 well round-bottom plates (Corning 25850) using 100 μl/well of media as a diluent. Next, 100 μl volumes of $^{51}$Cr-labeled (see below) targets [E.G7 (OVA)-an ovalbumin gene transfected EL4 cell line] at $1 \times 10^5$ cells/ml were added to the wells. Spontaneous release. (SR) wells contained 100 μl of targets and 100 μl of media. Maximal release (MR) wells contained 100 μl of targets and 100 μl detergent (2% Tween 20). Effector/target (E/T) ratios were 50:1, 25:1, 12.5:1, 6.25:1. The plates were centrifuged at 400×g and incubated at 37° C., 5% $CO_2$ for 4 hr. After the incubation the well supernatants were collected using a Skatron Supernatant Collection System.
Percent specific lysis=

$$100 \times \left[ \frac{(Exp.Release - SR)}{(MR - SR)} \right]$$

Target cells, E.G7 (OVA), were labeled with $^{51}$Cr (sodium chromate) as follows. In a total volume of 1.0 ml were mixed $5 \times 10^6$ target cells and 250 μCi $^{51}$Cr in 15 ml conical tube. The cell suspensions were incubated in a 37° C. water bath for 90 min., with gentle mixing every 15 min. After incubation the labeled cells were washed 3× by centrifugation and decanting with 15 ml volumes of media. After the third centrifugation the cells were resuspended in 10 ml of fresh media and allowed to stand at room temperature for 30 min. and then centrifuged. The cells were finally resuspended in media to $1 \times 10^5$ cells/ml. The results of the cytotoxicity assay are presented in Tables 2 and 3.

TABLE 2

Cytotoxic Response 14d post 1°

| Adjuvant | MLA μg | % Cytotoxicity E/T | | | |
|---|---|---|---|---|---|
| | | 50:1 | 25:1 | 12.5:1 | 6.25:1 |
| Pre-diluted day 7 | 3D-MLA/SE | 50 | 44 | 30 | 18 | 7 |
| | 3D-MLA/SE | 25 | 36 | 17 | 11 | 6 |
| | 3D-MLA/SB | 5 | 29 | 13 | 9 | 4 |
| | 3D-MLA/SE | 1 | 27 | 13 | 7 | 3 |
| | SE(Vehicle) | 0 | 25 | 13 | 7 | 4 |
| | PBS | 0 | 7 | 5 | 2 | 0 |
| Diluted day 0 | 3D-MLA/SE | 50 | 21 | 12 | 5 | 3 |
| | 3D-MLA/SE | 25 | 48 | 36 | 24 | 13 |

TABLE 2-continued

Cytotoxic Response 14d post 1°

| Adjuvant | MLA μg | % Cytotoxicity E/T | | | |
|---|---|---|---|---|---|
| | | 50:1 | 25:1 | 12.5:1 | 6.25:1 |
| 3D-MLA/SE | 5 | 22 | 14 | 9 | 4 |
| 3D-MLA/SE | 1 | 25 | 14 | 7 | 3 |
| SE(Vehicle) | 0 | 24 | 11 | 6 | 3 |
| PBS | 0 | 8 | 3 | 1 | 0 |
| Normal | — | 6 | 3 | 2 | 0 |

TABLE 3

Cytotoxic Response day 14 post 2°

| | Adjuvant | MLA μg | % Cytotoxicity E/T | | | |
|---|---|---|---|---|---|---|
| | | | 50:1 | 25:1 | 12.5:1 | 6.25:1 |
| Pre-diluted day7 | 3D-MLA/SE | 50 | 89 | 65 | 41 | 25 |
| | 3D-MLA/SE | 25 | 79 | 64 | 40 | 23 |
| | 3D-MLA/SE | 5 | 64 | 45 | 27 | 16 |
| | 3D-MLA/SE | 1 | 44 | 30 | 18 | 8 |
| | SE(Vehicle) | 0 | 65 | 39 | 31 | 18 |
| | PBS | 0 | 28 | 18 | 10 | 6 |
| Diluted day 0 | 3D-MLA/SE | 50 | 80 | 56 | 39 | 26 |
| | 3D-MLA/SE | 25 | 77 | 48 | 31 | 18 |
| | 3D-MLA/SE | 5 | 86 | 68 | 43 | 28 |
| | 3D-MLA/SE | 1 | 63 | 36 | 23 | 11 |
| | SE(Vehicle) | 0 | 63 | 42 | 28 | 14 |
| | PBS | 0 | 17 | 12 | 7 | 4 |
| | Normal | — | 7 | 2 | 0 | 0 |

B) Administration of 3D-MLA/SE and a protein antigen induced both a cytotoxic T-lymphocyte response and antigen production in treated mice. BALB/c mice were immunized subcutaneously with 2.0 μg HbsAg+25 μg 3D-MLA/SE on day 0(1°) and day 21 (20°). CTL assays were conducted as above. 3D-MLA/SE adjuvant was prepared as in Example 1. Table 4 illustrates a cytotoxic T-lymphocyte response was inducted.

TABLE 4

Cytotoxic Response

| Adjuvant | Day | % Cytotoxicity E/T | | | |
|---|---|---|---|---|---|
| | | 50:1 | 25:1 | 12.5:1 | 6.25:1 |
| 3D-MLA/SE | d17 post 1° | 55 | 27 | 14 | 10 |
| Vehicle SE | | 32 | 16 | 9 | 6 |
| 3D-MLA/SE | d16 post 2° | 81 | 62 | 47 | 24 |
| Vehicle SE | | 38 | 23 | 14 | 8 |

The results of the antibody titer to HbsAg are shown in Table 5. Sera from bleeds taken on day 28 post 2° were titered on ELISA plates coated with either HbsAg or a 28 amino acid peptide (p72) which contains B-cell epitopes found in the S-region, residues 110–137, of the HbsAg.

TABLE 5

Anti-hepatitis antibody titer in treated mice.

| | Anti-HBsAg Titer[-1] | | | |
|---|---|---|---|---|
| | HBsAg | | p72-peptide | |
| Adjuvant | IgG$_1$ | IgG$_{2a}$ | IgG$_1$ | IgG$_{2a}$ |
| 3D-MLA/SE | 1024 K | 2048 K | 64 K | 256 K |
| Vehicle SE | 1024 K | 64 K | 64 K | 4 K |
| Normal Mouse Serum | <0.5 K | <0.5 K | <0.5 K | <0.5 K |

Mice treated with 3D-MLA/SE displayed both humoral and cytotoxic T-lymphocyte responses to the hepatitis B surface antigen.

EXAMPLE 4

Evaluation of 3D-MLA/SE for Pyrogenicity

3D-MLA/SE adjuvant was evaluated in the standard three rabbit USP pyrogen test (NAMSA, Northwood Ohio). 3D-MLA/SE adjuvant of the present invention was compared to 3D-MLA formulated in 40% propylene glycol (PG) and 10% ethanol (EtOH) which was evaluated at dose levels of 5, 8, 11, 14, 15, 17, 20, 25, 30, 35 μg/kg over two experimental runs. The 3D-MLA/SE formulation was evaluated in the same rabbit pyrogen test at dose levels of 75, 1,00, 125, 150, 200, 250, 300, 350 μg/kg over two experimental runs. Pyrogenic doses and borderline pyrogenic doses were defined by established USP definitions. A borderline pyrogenic dose was a dose where at least one of three rabbits had a peak temperature rise of $\geq 0.5°$ C. above baseline over three hours postdosing.

TABLE 6A

Pyrogenicity of 3D-MLA in 40% PG/10% EtOH
MAXIMUM TEMPERATURE RISE

| Dose μg/Kg | Rabbit 1 | Rabbit 2 | Rabbit 3 | Total ° C. |
|---|---|---|---|---|
| 35 | 1.1 | 0.6 | 0.9 | 2.6 |
| 35 | 1.1 | 0.9 | 2.4 | 4.3 |
| 30 | 0.9 | 0.6 | 0.7 | 2.2 |
| 25 | 0.7 | 1.1 | 0.9 | 2.7 |
| 20 | 0.5 | 0.6 | 0.6 | 1.7 |
| 17 | 0.4 | 0.3 | 0.3 | 1.0 |
| 15 | 0.4 | 0.3 | 0.4 | 1.1 |
| 14 | 0.4 | 0.3 | 0.3 | 1.0 |
| 11 | 0.1 | 0.2 | 0.1 | 0.4 |
| 8 | 0.0 | 0.1 | 0.1 | 0.2 |
| 5 | 0.1 | 0.0 | 0.0 | 0.1 |

TABLE 6B

Pyrogenicity of 3D-MLA/SE
MAXIMUM TEMPERATURE RISE

| Dose μg/Kg | Rabbit 1 | Rabbit 2 | Rabbit 3 | Total ° C. |
|---|---|---|---|---|
| 350 | 0.7 | 0.6 | 0.8 | 2.1 |
| 350 | 0.3 | 0.6 | 0.6 | 1.5 |
| 300 | 0.8 | 0.7 | 0.6 | 2.1 |
| 250 | 0.4 | 0.5 | 0.3 | 1.2 |
| 200 | 1.0 | 1.0 | 1.1 | 3.1 |
| 200 | 0.2 | 0.1 | 0.1 | 0.4 |

TABLE 6B-continued

Pyrogenicity of 3D-MLA/SE
MAXIMUM TEMPERATURE RISE

| Dose μg/Kg | Rabbit 1 | Rabbit 2 | Rabbit 3 | Total ° C. |
|---|---|---|---|---|
| 150 | 0.3 | 0.2 | 0.2 | 0.7 |
| 150 | 0.1 | 0.3 | 0.2 | 0.6 |
| 125 | 0.1 | 0.1 | 0.1 | 0.1 |
| 100 | 0.1 | 0.2 | 0.1 | 0.4 |
| 75 | 0.0 | 0.1 | 0.1 | 0.2 |

3D-MLA/SE adjuvant was further evaluated for pyrogenicity and compared to 3D-MLA formulated in 10% EtOH.

TABLE 7

Pyrogenicity of 3D-MLA/SE vs. 3D-MLA in 10% EtOH
MAXIMUM TEMPERATURE RISE

| Material | Dose μg/Kg | Rabbit 1 | Rabbit 2 | Rabbit 3 | Total ° C. |
|---|---|---|---|---|---|
| 3D-MLA/EtOH | 10 | 1.5 | 1.5 | 1.5 | 4.5 |
| 3D-MLA/EtOH | 5 | 0.7 | 0.9 | 0.4 | 2.0 |
| 3D-MLA/EtOH | 2.5 | 0.3 | 0.4 | 0.1 | 0.8 |
| 3D-MLA/EtOH | 2.5 | 0.1 | 0.2 | 0.1 | 0.4 |
| 3D-MLA/EtOH | 1.25 | 0.0 | 0.0 | 0.0 | 0.0 |
| 3D-MLA/SE | 200 | 0.6 | 0.6 | 1.0 | 2.2 |
| 3D-MLA/SE | 150 | 0.5 | 0.2 | 0.4 | 1.1 |
| 3D-MLA/SE | 100 | 0.2 | 0.3 | 0.1 | 0.6 |
| 3D-MLA/SE | 50 | 0.0 | 0.0 | 0.0 | 0.0 |
| 3D-MLA/SE | 75 | 0.1 | 0.1 | 0.3 | 0.5 |
| 3D-MLA/SE | 50 | 0.0 | 0.2 | 0.0 | 0.2 |
| 3D-MLA/SE | 35 | 0.3 | 0.1 | 0.1 | 0.5 |
| 3D-MLA/SE | 20 | 0.0 | 0.0 | 0.0 | 0.0 |
| 3D-MLA/SE | 10 | 0.0 | 0.0 | 0.1 | 0.1 |
| 3D-MLA/SE | 0 | 0.4 | 0.0 | 0.0 | 0.4 |

There is a tenfold differential in pyrogenicity with a 20 μg/kg dose of 3D-MLA in 40% PG/10% EtOH being borderline pyrogenic, and a dose of 200 μg/kg for. 3D-MLA/SE defined as a threshold pyrogenic dose. 3D-MLA/SE adjuvant was considerably less pyrogenic that other formulations of the compound (Tables 6 and 7). Likewise, the adjuvant composition of the subject invention is safe producing drug-related lesions that are minimal to none at injection sites, lymph nodes draining the injection sites and spleens.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An adjuvant composition comprising a metabolizable oil, one or more surfactants, an antioxidant and a component to make said composition isotonic, wherein said composition is an oil-in-water emulsion and said emulsion has a hydrophobic-lipophilic balance of about 8.0.

2. An adjuvant composition comprising a metabolizable oil, one or more surfactants, an antioxidant, a component to make said composition isotonic, and an attenuated lipid A derivative.

3. The adjuvant composition of claim 2, wherein said attenuated lipid A derivative is selected from the group consisting of monophosphoryl lipid A and 3-deacylated monophosphoryl lipid A.

4. The adjuvant composition of claim 3, wherein said attenuated lipid A derivative is monophosphoryl lipid A.

5. The adjuvant composition of claim 3, wherein said attenuated lipid A derivative is 3-deacylated monophosphoryl lipid A.

6. The adjuvant composition of claim 3, wherein said attenuated lipid A derivative is about 1.200% to about 0.005% weight to volume of said composition.

7. A vaccine composition comprising an antigen and an adjuvant composition comprising a metabolizable oil, one or more surfactants, an antioxidant and a component to make said composition isotonic, wherein said composition comprises about 10% volume to volume squalene, 0.09% weight to volume poloxamer 188, 1.9% weight to volume egg phosphatidyl choline, 1.75% volume to volume glycerol and 0.05% weight to volume a tocopherol.

* * * * *

UNITED STATES PATENT AND TRADEMARK OFFICE
CERTIFICATE OF CORRECTION

PATENT NO. : 6,630,161 B1
DATED : October 7, 2003
INVENTOR(S) : Leesman

It is certified that error appears in the above-identified patent and that said Letters Patent is hereby corrected as shown below:

Column 12,
Line 6, replace "a tocopherol" with -- *a* tocopherol --.

Signed and Sealed this

Sixth Day of July, 2004

JON W. DUDAS
*Acting Director of the United States Patent and Trademark Office*